(12) United States Patent
Kabot et al.

(10) Patent No.: US 9,987,490 B2
(45) Date of Patent: Jun. 5, 2018

(54) REAL TIME COCHLEAR IMPLANT INSERTION STATUS INDICATOR

(71) Applicant: MED-EL Elektromedizinische Geraete GmbH, Innsbruck (AT)

(72) Inventors: Ernst Kabot, Innsbruck (AT); Mathias Kals, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 211 days.

(21) Appl. No.: 14/700,647

(22) Filed: Apr. 30, 2015

(65) Prior Publication Data

US 2015/0314122 A1 Nov. 5, 2015

Related U.S. Application Data

(60) Provisional application No. 61/987,715, filed on May 2, 2014.

(51) Int. Cl.
*A61N 1/36* (2006.01)
*A61N 1/08* (2006.01)
*A61N 1/05* (2006.01)

(52) U.S. Cl.
CPC ........... *A61N 1/36036* (2017.08); *A61N 1/08* (2013.01); *A61N 1/0541* (2013.01)

(58) Field of Classification Search
CPC ..... A61N 1/0541; A61N 1/08; A61N 1/36032
See application file for complete search history.

(56) References Cited

U.S. PATENT DOCUMENTS

| 6,112,124 A | 8/2000 | Loeb |
| 9,352,153 B2 * | 5/2016 | van Dijk .............. A61N 1/0541 |
| 2006/0235332 A1 * | 10/2006 | Smoorenburg .... A61N 1/37247 600/559 |
| 2011/0087085 A1 | 4/2011 | Tsampazis et al. ........... 600/379 |
| 2012/0191161 A1 | 7/2012 | van Dijk ........................ 607/57 |
| 2012/0316454 A1 | 12/2012 | Carter |

FOREIGN PATENT DOCUMENTS

| EP | 1754509 A1 | 2/2007 | .............. A61N 1/36 |
| WO | WO 2016/035027 A1 | 3/2016 | |

OTHER PUBLICATIONS

International Searching Authority, International Search Report—International Application No. PCT/US2015/028482, dated Jul. 29, 2015, together with the Written Opinion of the International Searching Authority, 13 pages.
European Patent Office, Extended European Search Report, Application No. 15786013.1, 8 pages, dated Sep. 20, 2017.

* cited by examiner

*Primary Examiner* — Amanda Patton
(74) *Attorney, Agent, or Firm* — Sunstein Kann Murphy & Timbers LLP

(57) ABSTRACT

A method of determining insertion status of a cochlear implant electrode array into a cochlea of a patient is provided. The method includes measuring conductivity associated with an electrode in the electrode array. Insertion status of the electrode is determined based, at least in part, on the measured conductivity.

23 Claims, 4 Drawing Sheets

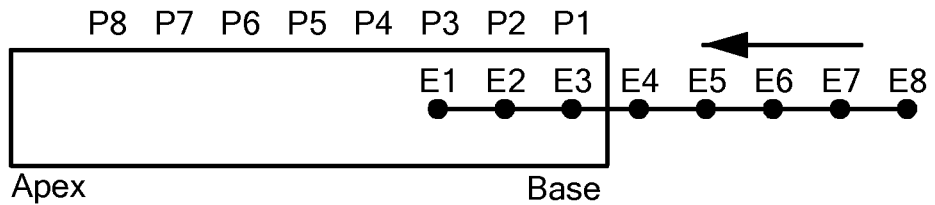
FIG. 6
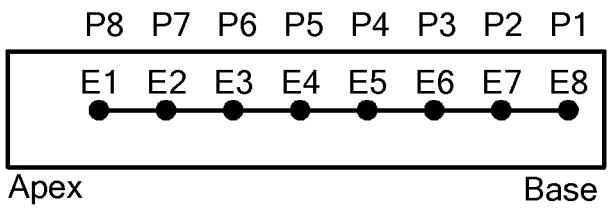
FIG. 7
| | E1 | E2 | E3 | E4 | E5 | E6 | E7 | E8 |
|---|---|---|---|---|---|---|---|---|
| t1 | $Z_{1,1}$ | 8 | 8 | 8 | 8 | 8 | 8 | 8 |
| t2 | $Z_{1,2}$ | $Z_{2,1}$ | 8 | 8 | 8 | 8 | 8 | 8 |
| t3 | $Z_{1,3}$ | $Z_{2,2}$ | $Z_{3,1}$ | 8 | 8 | 8 | 8 | 8 |
| t4 | $Z_{1,4}$ | $Z_{2,3}$ | $Z_{3,2}$ | $Z_{4,1}$ | 8 | 8 | 8 | 8 |
| t5 | $Z_{1,5}$ | $Z_{2,4}$ | $Z_{3,3}$ | $Z_{4,2}$ | $Z_{5,1}$ | 8 | 8 | 8 |
| t6 | $Z_{1,6}$ | $Z_{2,5}$ | $Z_{3,4}$ | $Z_{4,3}$ | $Z_{5,2}$ | $Z_{6,1}$ | 8 | 8 |
| t7 | $Z_{1,7}$ | $Z_{2,6}$ | $Z_{3,5}$ | $Z_{4,4}$ | $Z_{5,3}$ | $Z_{6,2}$ | $Z_{7,1}$ | 8 |
| t8 | $Z_{1,8}$ | $Z_{2,7}$ | $Z_{3,6}$ | $Z_{4,5}$ | $Z_{5,4}$ | $Z_{6,3}$ | $Z_{7,2}$ | $Z_{8,1}$ |
FIG. 8

REAL TIME COCHLEAR IMPLANT INSERTION STATUS INDICATOR

CROSS-REFERENCE TO RELATED APPLICATIONS

This application claims the benefit of provisional application U.S. Ser. No. 61/987,715, entitled "Real Time Cochlear Implant Insertion Status Indicator," filed May 2, 2014, the disclosure of which is hereby incorporated herein by reference in its entirety.

TECHNICAL FIELD

The present invention relates to cochlear implants, and more particularly, to a real time system and methodology for detecting the insertion depth of an electrode within the cochlea.

BACKGROUND ART

A normal ear transmits sounds as shown in FIG. 1 through the outer ear 101 to the tympanic membrane (eardrum) 102, which moves the bones of the middle ear 103 (malleus, incus, and stapes), which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea. In such cases a cochlear implant is an auditory prosthesis which uses an implanted stimulation electrode to bypass the acoustic transducing mechanism of the ear and instead stimulate auditory nerve tissue directly with small currents delivered by multiple electrode contacts distributed along the electrode.

FIG. 1 also shows some components of a typical cochlear implant system which includes an external microphone that provides an audio signal input to an external signal processing stage 111 where various signal processing schemes can be implemented. The processed signal is then converted into a digital data format, such as a sequence of data frames, for transmission into the implant stimulator 108. Besides extracting the audio information, the implant stimulator 108 also performs additional signal processing such as error correction, pulse formation, etc., and produces a stimulation pattern (based on the extracted audio information) that is sent through connected wires 109 to an electrode array 110 inserted into the cochlea. Typically, this electrode array 110 includes multiple electrode contacts on its surface that provide selective stimulation of the cochlea 104. Stimulation is either carried out against an external reference electrode contact (i.e., a remote ground contact) outside the cochlea or against another electrode contact of the array within the cochlea 104.

The insertion of the electrode array 110 requires surgery. Cochlear implant manufacturers offer to surgeons a wide range of mechanical tools necessary for implantation of the device. However, since the electrode array 110 is inserted into the cochlea 104 through a small hole, the surgeon gets no visual conformation of the exact placement of the electrode array 110 within the cochlea 104 itself. Insertion depth may be estimated by the part of the electrode array 110 that has not yet been inserted into the cochlea 104 but apart from that, the exact location of already inserted contacts is unknown during surgery.

Imaging techniques, like X-ray or MRI, may be used to give information about the exact positioning of the electrode array 110. However, all of these methods require additional effort and equipment that is usually not available during surgery. Consequently, the imaging often happens at a later date, when a correction is no longer possible. Instead, electrode contacts will often have to be switched off from stimulation to compensate for a misplacement of the electrode array 110, which may lead to a reduced performance of the cochlear implant.

SUMMARY OF THE EMBODIMENTS

In accordance with an embodiment of the invention there is provided a method of determining insertion status of a cochlear implant electrode array into a cochlea of a patient. The method includes measuring conductivity associated with an electrode contact in the electrode array. Insertion status of the electrode contact is determined based, at least in part, on the measured conductivity.

In accordance with related embodiments of the invention, measuring conductivity associated with an electrode contact in the electrode array may include measuring an electrode impedance value (EIV) associated with the electrode contact, or performing an ECAP measurement. The electrode impedance value (EIV) of the electrode contact may be measured between the electrode contact and a remote ground electrode, and/or between the electrode contact and a different electrode contact in the electrode array.

In accordance with further related embodiments of the invention, determining the insertion status of the electrode contact may include comparing the electrode impedance value (EIV) of the electrode contact to a threshold value. For example, that the electrode impedance value (EIV) of the electrode contact increases or decreases past the threshold value may indicate that the electrode contact has been inserted into the cochlea. An indication on a user interface may be provided if the electrode contact has been inserted into the cochlea. The indication may be updated periodically. For example, the indication may be updated substantially in real time, such as, without limitation, on the order of milliseconds or less, or in various embodiments in excess of a second, but less than two to three seconds.

In accordance with still further related embodiments of the invention, the method may include stimulating an electrode contact inserted into the cochlea, and measuring voltage or current between the stimulated electrode contact and one or more other electrode contacts inserted into the cochlea. Based at least on the measured voltage or current, the occurrence of an event associated with insertion of the electrode array may be determined, such as an tip fold-over, a buckling or a loop. The method may include determining presence of air bubbles associated with an inserted electrode contact.

In accordance with yet further related embodiments of the invention, the method may include sequentially inserting each of the electrode contacts of the electrode array into the cochlea of the patient, wherein after insertion of each electrode contact, conductivity of each electrode contact is measured, and the insertion status of each electrode contact is determined.

In accordance with another embodiment of the invention, a system for determining insertion status of a cochlear implant is provided. The system includes an electrode array associated with a cochlear implant for stimulating the acoustic nerve of a patient. The system further includes a means for measuring conductivity associated with an electrode contact in the electrode array, and means for determining insertion status of the electrode contact into the cochlea of a patient based, at least in part, on the measured conductivity.

In accordance with related embodiments of the invention, the means for measuring may include means for measuring an electrode impedance value (EIV) associated with the electrode contact. The means for determining the insertion status of the electrode contact may include means for comparing the electrode impedance value (EIV) of the electrode contact to a threshold value. For example, that the electrode impedance value (EIV) of the electrode contract increases or decreases past the threshold value may indicate that the electrode contact has been inserted into the cochlea. A user interface may be provided, that includes, for example, an indication if the electrode contact has been inserted into the cochlea. The indication may be updated periodically. For example, the indication may be updated substantially in real time, such as, without limitation, on the order of milliseconds or less, or in various embodiments in excess of a second, but less than two to three seconds.

In accordance with still further related embodiments of the invention, the system may include means for stimulating an electrode contact inserted into the cochlea, and means for measuring voltage or current between the stimulated electrode contact and one or more other electrode contacts inserted into the cochlea. The system may further include means for determining, based at least on the measured voltage or current, whether an event selected from group consisting of a tip fold-over, a buckling and a loop associated with the electrode array has occurred. The system may include means for determining presence of air bubbles associated with an inserted electrode.

In accordance with another embodiment of the invention, a system for determining insertion status of a cochlear implant includes an electrode array associated with a cochlear implant for stimulating the acoustic nerve of a patient. An external controller is operatively coupled to the electrode array, the external controller configured to measure conductivity associated with an electrode contact in the electrode array, and determine insertion status of the electrode contact into the cochlea of a patient based, at least in part, on the measured conductivity.

In accordance with related embodiments of the invention, the external controller may be configured to measure an electrode impedance value (EIV) associated with the electrode contact. The system may include a remote ground electrode, wherein the external controller is configured to measure the electrode impedance value (EIV) of the electrode contact by measuring the electrode impedance value (EIV) between the electrode contact and the remote ground electrode. The external controller may be configured to measure the electrode impedance value (EIV) of the electrode contact by measuring impedance between the electrode contact and a different electrode contact in the electrode array.

In accordance with further related embodiments of the invention, the system may include a user interface. The user interface may include an indication if it is determined that the electrode contact has been inserted into the cochlea. The external controller may be configured to stimulate an electrode contact inserted into the cochlea, and measure voltage and/or current between the stimulated electrode contact and one or more other electrode contacts inserted into the cochlea. The external controller may be configured, based at least on the measured voltage or current, to determine whether an event selected from the group consisting of a tip fold-over, a buckling and a loop associated with insertion of the electrode array has occurred.

BRIEF DESCRIPTION OF THE DRAWINGS

The foregoing features of embodiments will be more readily understood by reference to the following detailed description, taken with reference to the accompanying drawings, in which:

FIGS. 3-7 demonstrate the insertion of an eight-contact cochlear implant electrode array into a cochlea of a patient, in accordance with an embodiment of the invention. More particularly, FIG. 3 shows all electrode contacts E1-E8 outside the cochlea at time $t_0$. FIG. 4 shows the insertion of electrode contact E1 into the cochlea at time $t_1$. FIG. 5 shows the insertion of electrode contact E2 into the cochlea at time $t_2$. FIG. 6 shows the insertion of electrode contact E3 into the cochlea at time $t_3$. FIG. 7 shows all electrode contacts E1-E8 of the electrode contact array inserted into the cochlea at time $t_8$.

FIG. 8 shows an example of an impedance matrix that includes data collected during the insertion of the electrode array, in accordance with an embodiment of the invention.

DETAILED DESCRIPTION OF SPECIFIC EMBODIMENTS

In illustrative embodiments, a system and method of detecting the insertion depth of an electrode array within the cochlea is provided, that may be used during surgery in real time without the use of additional imaging devices. Foldovers and bucklings of the electrode array may be detected in real time, allowing for prompt correction by the surgeon. The system and method may also allow one to discriminate between high impedances caused by air bubbles and high impedances caused by tissue anomalies. Details are discussed below.

Figure 2:
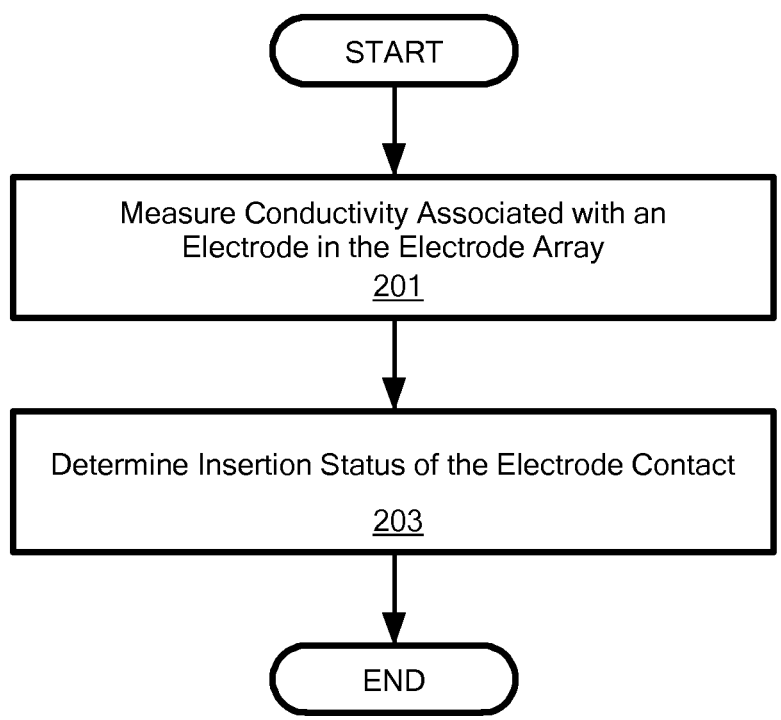
FIG. 2 shows a flow chart illustrating a method of detecting the insertion depth of an electrode array with a cochlear implant patient's cochlea, in accordance with an embodiment of the invention.

FIG. 2 shows a flow chart illustrating a method of detecting the insertion depth of an electrode array with a cochlear implant patient's cochlea, in accordance with an embodiment of the invention. The method makes use of the differences in conductivity of the various environments that may be in contact with the electrode array. More specifically, the cochlear ducts where the electrode array is to be inserted are filled with perilymph, a fluid with high conductivity. However, the middle ear from where the insertion is carried out is filled with air, which is characterized by very low or zero conductivity.

The method includes measuring conductivity associated with an electrode in the electrode array, step 201. In illustrative embodiments, electrode impedance values (EIV) may be measured or otherwise determined in monopolar mode between the electrode contacts of the electrode array and/or, without limitation, a remote ground electrode (RG). Alternatively, EIVs may be measured in bipolar mode, such as between contacts of the electrode array that are identified as being inserted, and an electrode contact that is just to be inserted. It is to be understood that other measurements known in the art may be taken instead of EIVs, such as electrically evoked compound action potential (ECAP) measurements.

Figure 1:
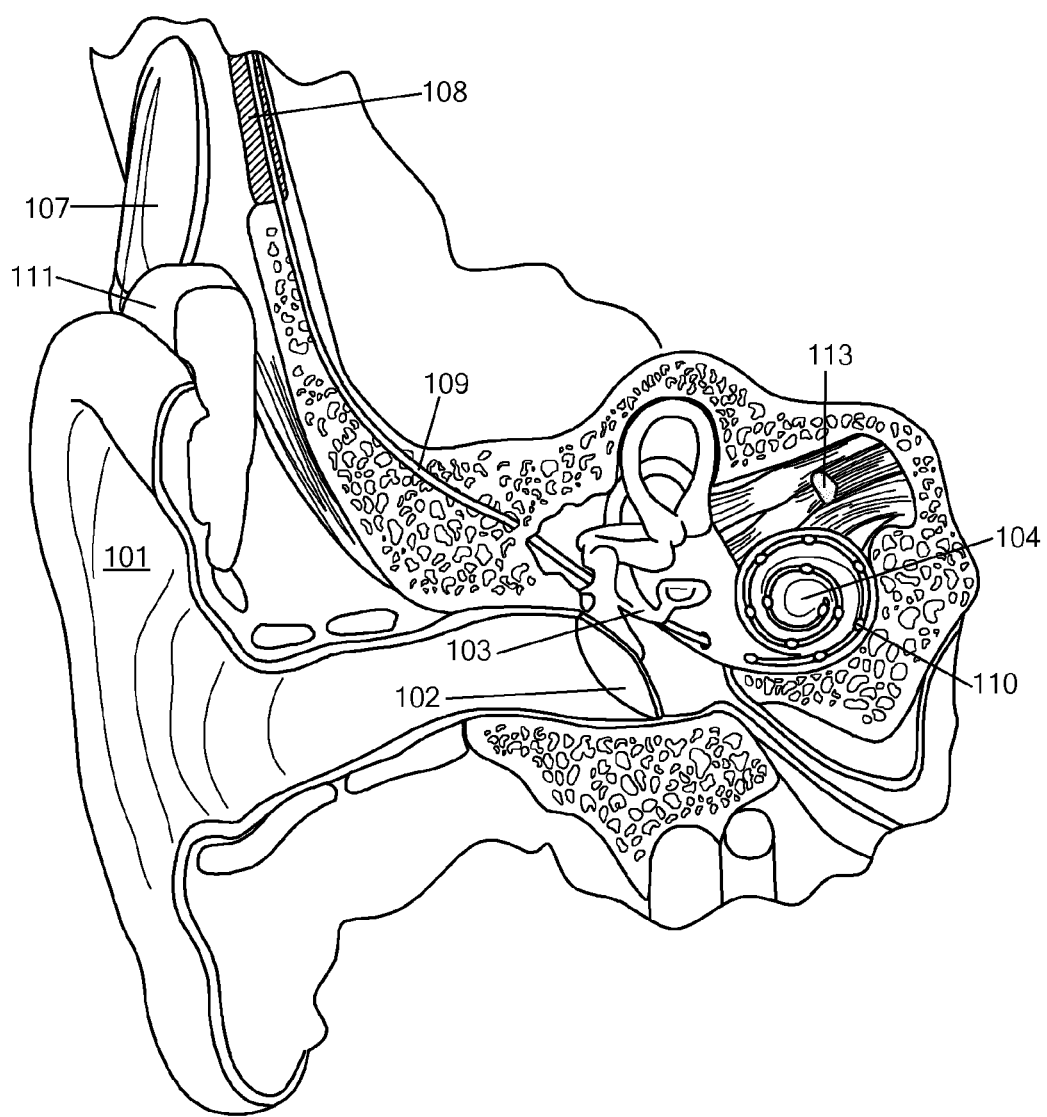
FIG. 1 shows various anatomical structures of the human ear and components of a typical cochlear implant system in relation thereto.

Referring back to FIG. 1, the impedance measurement(s) may be made, in part, by supplying stimulation signals (e.g., current or voltage) to an electrode contact in the electrode array 110. The stimulation signals may be initiated by an external controller operatively coupled to the electrode array, either directly, or via the cochlear implant's processor stage 111 (which may be external, or implanted in the case of a fully implanted cochlear implant) and/or stimulator 108. The transmission or retrieval of data to and from the implanted portion of the cochlear implant (e.g., the stimulator 108 and electrode array 110) may require an external coil to be placed proximate a coil associated with the implanted portion of the cochlear implant during electrode array insertion.

As described in more detail below, the system may be configured to periodically monitor EIVs during electrode contact insertion. Some level of user interaction with the system may be needed. For example, the user may need to initiate and/or confirm any measurements via a user interface on, without limitation, the external controller.

The insertion status of the electrode contact may then be determined based, at least in part, on the measured conductivity, step 203. This step may be performed, without limitation, at the external controller. The EIV of an electrode contact fully inserted into the cochlea will be much lower than the EIV of a contact that is not yet inserted but still outside of the cochlea. In various embodiments, the determination of the insertion status may include comparing the measured EIV status to a threshold value. For example, if the EIV associated with an electrode contact drops below a predefined threshold, the electrode contact may be considered properly inserted.

The insertion status may be provided on a user interface, such as, without limitation, a display associated with the external controller. Insertion status may include whether the electrode contact has been fully inserted, or whether a problem has arisen, such as an electrode tip fold-over, buckling or loop has occurred, or an air bubble, as described in more detail below. To provide useful feedback to the surgeon, the determination of the insertion status may be performed in real-time or at least with a time resolution that will be perceived as such. For example, the status update may be updated at, without limitation, 10 Hz or greater. The status update provided on the user interface may include a graphical illustration.

FIGS. 3-7 demonstrate the insertion of an eight-contact cochlear implant electrode array into a cochlea of a patient, in accordance with an embodiment of the invention. Determination of the insertion status is performed in this embodiment using, without limitation, continuous measurements between electrode contacts Ei and a remote ground electrode (RG), where i denotes the index or the position of an electrode contact along the array. It is to be understood that the electrode array is not limited to eight electrode contacts, and may have any number of contacts.

Figure 3:
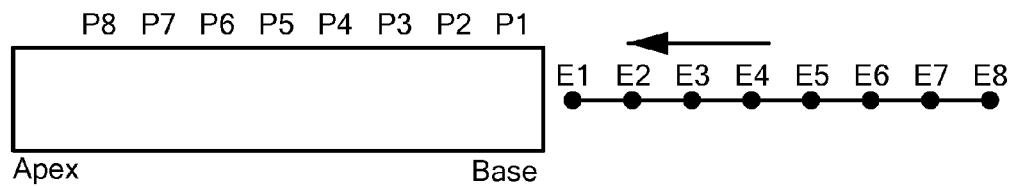

Prior to insertion at time $t_0$, all electrode contacts E1-E8 are outside the cochlea, surrounded by air, as shown in FIG. 3. The resulting impedance measurements for all the electrode contacts E1-E8 show high or infinite impedances.

Figure 4:
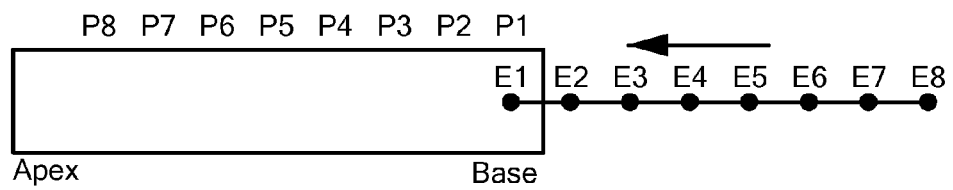

With the insertion of electrode contact E1 into the cochlea at time $t_1$, as shown in FIG. 4, the surrounding environment of this contact changes from air to perilymph. As a result, from a certain position P1 on, the impedance measured between E1 and RG will drop from very high or infinite to below a predefined threshold $Z_{thres}$, for example $Z_{thres}$=30 kOhms. Thus, at $t_1$ this contact can be characterized as inserted. The impedances between all other contacts outside the cochlea and RG are still infinite. The same holds true for impedances between electrode contacts E1 to E8. The impedance $Z_{1,1}$ (where the first index denotes the electrode number and the second the position) between E1 and RG measured at the time $t_1$ respectively at position P1 may be saved for later analysis (along with the impedances between electrode contacts E1 to E8, if desired).

Figure 5:
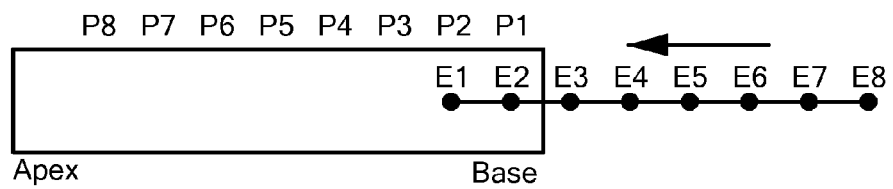

Further inserting the electrode array at a time $t_2$ results in detectable impedance of less than $Z_{thres}$ at electrode contact E2. Upon detecting that the impedance at electrode contact E2 is below the threshold $Z_{thres}$, it can be assumed that E2 has now reached position P1, as shown in FIG. 5. E2 can thus be characterized as inserted into the cochlea. The impedance $Z_{2,1}$ of E2 at position P1 may be saved.

As the whole electrode array has been inserted deeper into the cochlea at time $t_2$, electrode contact E1 has reached a position defined as P2. The impedance $Z_{1,2}$ between E1 and RG may be measured and saved. Note that since both E1 and E2 are inserted into the cochlea and completely surrounded by perilymph, the impedance between electrodes E1 and E2 has also dropped from infinite to a detectable value (this value may also be saved).

Further inserting the electrode array, electrode contact E3 becomes completely inserted into the cochlea at time $t_3$, as shown in FIG. 6. The impedance $Z_{3,1}$ measured between E3 and RG drops below the threshold $Z_{thres}$ and may be stored. In addition the impedances $Z_{2,2}$ at E2, now located at P2, and $Z_{1,3}$ at E1, located at P3, are also saved. Note that since both E1 and E2 are inserted into the cochlea and completely surrounded by perilymph, the impedances between electrodes E1, E2 and E3 have also dropped from infinite to a detectable value (these values may also be saved).

After three electrode contacts have been inserted into the cochlea, additional impedance measurements may be performed for the detection of, without limitation, tip fold-overs and bucklings along the inserted part of the electrode array. The voltage profile measured along a correctly inserted electrode array will decrease monotonically with increasing distance from the stimulating electrode when measured at neighboring electrode contacts. When measured at larger distances, cross-talk between different turns of the cochlea may appear. However, in the neighboring region of a stimulating electrode contact the voltages will drop for correctly inserted electrode arrays.

Illustratively, for the detection of misplaced electrode arrays, monopolar stimulation pulses may be generated at an inserted electrode contact $E_i$, and voltage measurements $U_{i+1}$ to $U_n$ are performed at other inserted contacts $E_{i+1}$ to $E_{i+2}$, with n being the greatest index of the inserted electrode contacts, and $1 \leq i \leq n-2$. In case of a tip fold-over, buckling or loop, the relation $U_{i+1} > U_{i+2}$ will not be true for all i. A tip fold-over will be detected when stimulating the most apical electrode contact $E_1$. For exclusion of turn cross-talk effects, a moving window of a certain number m of neighboring electrodes may be utilized to perform measurements within the n inserted electrodes (m<n). In the event of a tip fold-over or loop detection, the surgeon may advantageously receive instantaneous feedback, allowing for immediate correction of the electrode array positioning.

With continuing insertion, more and more electrodes of the array are identified as inserted into the cochlea, until finally all electrode contacts E1 to E8 are characterized accordingly, as shown in FIG. 7. In various embodiments, the impedances have been saved for each electrode contact at distinct positions P1 to P8 at the times $t_1$ to $t_8$.

In various embodiments, instead of determining the voltage drop from apical to basal contacts, the direction may also be from basal to apical, or it may be performed in both directions simultaneously. In case of a tip fold-over, buckling or loop, the relation $U_{i+1} > U_{i+2}$ for apical to basal direction with $1 \leq i \leq n-2$ and $U_{i-1} > U_{i-2}$ for basal to apical direction with $3 \leq i \leq n$ will not be true for all i. Instead of determining the voltage drop at two neighboring electrode contacts, another number of neighboring contacts may be used.

An example of data that may be collected during the insertion of the electrode array is the impedance matrix shown in FIG. 8, in accordance with an embodiment of the invention. More particularly, the matrix shown in FIG. 8 shows impedances of an exemplary electrode array having eight electrode contacts, measured between electrode contacts E1 to E8 and Remote Ground (RG) during insertion of the electrode contact array at times $t_1$-$t_8$. Data connected with a straight line are measured at the same location Pi, i=1, 2, ..., 8 within the cochlea. Prior to insertion, impedances are infinite as can be seem in the upper right half of the matrix. After insertion, the impedances $Z_{i,j}$ are less than $Z_{thres}$, where $Z_{i,j}$ denotes the impedance Z of electrode contact Ei at the position Pj. Data measured at the same position Pj is connected via diagonal lines.

The matrix representation shown in FIG. 8 may be used for distinguishing air bubbles, which seal electrode contacts from high tissue impedances at a certain location within the cochlea, in accordance with various embodiments of the invention. Illustratively, if an air bubble blocks the current flow of a single contact $E_k$, all data located in the corresponding column k will show higher impedance values than the data of neighboring columns. In this case the impedance may be comparable to the impedance prior to insertion, i.e. may not or not significantly drop after insertion but stay the same. In contrast, high tissue impedance at a distinct position $P_1$ within the cochlea would be measured at any electrode contact passing this position. In the matrix representation, high impedances would occur along the diagonal line $P_1$.

The above-described system/methodology allows for the determination of the insertion status of an electrode array in real-time, and may not only be provided to a surgeon but also to technical staff supervising the technical integrity of the implant and its electrode array. In various embodiments, the inter-electrode-impedances may be continuously monitored during insertion of the electrode array so as to evaluate the integrity of implant and electrode contact array. In this manner, tip fold-overs, bucklings or loops may be detected substantially immediately (depending on the status update rate), allowing for the straightening of the electrode array and ensuring correct placement of the electrode array. Air bubbles causing high impedance will be distinguished from tissue variations that may also result in high impedances. This information may be used to optimize the parameter setting of intra-operatively performed ECAP measurements.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of determining insertion status of a cochlear implant electrode array into a cochlea of a patient, the method comprising:

measuring conductivity associated with an electrode contact in the electrode array;

determining insertion status of the electrode contact based, at least in part, on the measured conductivity;

stimulating an electrode contact inserted into the cochlea, and measuring voltage or current between the stimulated electrode contact and one or more other electrode contacts inserted into the cochlea;

determining, based at least on the measured voltage or current, whether an event selected from the group consisting of a tip fold-over, a buckling and a loop associated with insertion of the electrode array has occurred; and determining presence of air bubbles associated with an inserted electrode contact.

2. The method according to claim 1, wherein measuring conductivity includes measuring an electrode impedance value (EIV) associated with the electrode contact.

3. The method according to claim 2, wherein measuring the electrode impedance value (EIV) of the electrode contact includes measuring the electrode impedance value (EIV) between the electrode contact and a remote ground electrode.

4. The method according to claim 2, wherein measuring the electrode impedance value (EIV) of the electrode contact includes measuring impedance between the electrode contact and a different electrode contact in the electrode array.

5. The method according to claim 2, wherein determining the insertion status of the electrode contact includes comparing the electrode impedance value (EIV) of the electrode contact to a threshold value.

6. The method according to claim 1, further including providing an indication on a user interface if it is determined that the electrode contact has been inserted into the cochlea.

7. The method according to claim 1, further comprising:
sequentially inserting each of the electrode contacts of the electrode array into the cochlea of the patient, wherein after insertion of each electrode contact, conductivity of each electrode contact is measured, and the insertion status of each electrode contact is determined.

8. The method according to claim 1, further comprising:
inserting, at least partially, the electrode array into the cochlea of the patient, wherein conductivity of the electrode contact is measured, and the insertion of the electrode is determined.

9. The method according to claim 1, wherein measuring conductivity of the electrode contact in the array includes performing an electrically evoked compound action potential (ECAP) measurement.

10. A method of determining insertion status of a cochlear implant electrode array into a cochlea of a patient, the method comprising:
sequentially inserting each of the electrode contacts of the electrode array into the cochlea of the patient, wherein after each insertion, the method further includes:
measuring conductivity of each electrode contact; and
determining the insertion status of each electrode contact based, at least in part, on the measured conductivity; and
determining presence of air bubbles associated with an inserted electrode contact.

11. The method according to claim 10, wherein measuring includes measuring an electrode impedance value (EIV) associated with the electrode contact.

12. The method according to claim 11, wherein measuring the electrode impedance value (EIV) of the electrode contact includes measuring the electrode impedance value (EIV) between the electrode contact and a remote ground electrode.

13. The method according to claim 11, wherein measuring the electrode impedance value (EIV) of the electrode contact includes measuring impedance between the electrode contact and a different electrode contact in the electrode array.

14. The method according to claim 11, wherein determining the insertion status of the electrode contact includes comparing the electrode impedance value (EIV) of the electrode contact to a threshold value.

15. The method according to claim 10, further including providing an indication on a user interface if it is determined that the electrode contact has been inserted into the cochlea.

16. The method according to claim 10, further comprising stimulating an electrode contact inserted into the cochlea, and measuring voltage or current between the stimulated electrode contact and one or more other electrode contacts inserted into the cochlea.

17. The method according to claim 10, wherein measuring conductivity of the electrode contact in the array includes performing an electrically evoked compound action potential (ECAP) measurement.

18. A method of determining insertion status of a cochlear implant electrode array into a cochlea of a patient, the method comprising:
measuring conductivity associated with an electrode contact in the electrode array;
determining insertion status of the electrode contact based, at least in part, on the measured conductivity; and
determining presence of air bubbles associated with an inserted electrode contact.

19. The method according to claim 18, wherein measuring conductivity includes measuring an electrode impedance value (EIV) associated with the electrode contact.

20. The method according to claim 19, wherein determining the insertion status of the electrode contact includes comparing the electrode impedance value (EIV) of the electrode contact to a threshold value.

21. The method according to claim 19, wherein measuring the electrode impedance value (EIV) of the electrode contact includes measuring impedance between the electrode contact and a different electrode contact in the electrode array.

22. The method according to claim 18, further including providing an indication on a user interface if it is determined that the electrode contact has been inserted into the cochlea.

23. The method according to claim 18, wherein measuring conductivity of the electrode contact in the array includes performing an electrically evoked compound action potential (ECAP) measurement.

* * * * *